US006888014B2

(12) United States Patent
Huang et al.

(10) Patent No.: US 6,888,014 B2
(45) Date of Patent: May 3, 2005

(54) DAMMARANE SAPOGENINS, THEIR USE AS ANTI-CANCER AGENTS, AND A PROCESS FOR PRODUCING SAME

(75) Inventors: Dong Huang, Surrey (CA); Dong Feng Qi, Shenyang (CN)

(73) Assignee: PanaGin Pharmaceuticals Inc., Richmond (CA)

( * ) Notice: Subject to any disclaimer, the term of this patent is extended or adjusted under 35 U.S.C. 154(b) by 161 days.

(21) Appl. No.: 09/982,018

(22) Filed: Oct. 19, 2001

(65) Prior Publication Data

US 2003/0087836 A1 May 8, 2003

Related U.S. Application Data

(63) Continuation-in-part of application No. 09/910,887, filed on Jul. 24, 2001.

(51) Int. Cl.⁷ .......................... A61K 31/56; C07J 53/00; C07J 9/00; C07J 17/00
(52) U.S. Cl. .......................... 552/502; 552/540; 536/5; 514/169; 514/171; 514/180
(58) Field of Search ................................ 552/502, 540; 536/5; 514/169, 171, 180

(56) References Cited

U.S. PATENT DOCUMENTS

| | | | | |
|---|---|---|---|---|
| 4,157,894 A | * | 6/1979 | Bombardelli | ............. 23/230 R |
| 4,621,137 A | | 11/1986 | Miyake et al. | |
| 4,966,893 A | * | 10/1990 | Pang et al. | .................... 514/54 |
| 5,850,032 A | * | 12/1998 | Wann | ......................... 800/410 |
| 5,919,770 A | | 7/1999 | Hideo et al. | |

FOREIGN PATENT DOCUMENTS

| | | |
|---|---|---|
| JP | 8-208688 | 8/1996 |
| JP | 11-295310 | 10/1999 |
| WO | WO/97/31933 | 9/1997 |

OTHER PUBLICATIONS

Shibata, Shoji et al.; Chemical and Pharmaceutical Bulletin (1966), 14(6), 595–600.*
Jianbiao et al. (DN 120:279955, abstract of Lizi Jiaohuan Yu Xifu (1993), 9(2), 97–101).*
Y.S. Kim, et al., Ginsenoside Rh2 and Rh3 induce differentiation of HL–60 cells into granulo–cytes: modulation of protein kinase C isoforms during differentiation by ginseoside Rh2, The International Journal of Biochemistry & Cell Biology 30 (1998) 327–338.
A.S. Attele, et al., Ginseng Pharmacology: Multiple Constituents and Multiple Actions, Biochemical Pharmacology, vol. 58, pp. 1685–1693, 1999.
H. Hasegawa, et al., Reversal of Daunomycin and Vinblastine Resistance in Multidrug–Resistant P388 Leukemia in vitro through Enhanced Cytotoxicity by Triterpenoids, Planta Med. 61 (1995) 409–413.

www.herbmed.org/herbs/panax.htm, Alternative Medicine Foundation—information regarding ginseng.
Abstract—Y.N. Lee, et al., In vitro induction of differentiation by ginsenoides in F9 tetratocarcinoma cells, Eur. J. Cancer Jul. 1996; 32A(8):1420–8.
Abstract—S. Odashima, et al., Control of phenotypic expression of cultured B16 melanoma cells by plant glycosides, Cancer Res. Jun. 1985; 45(6):2781–4.
Abstract—L.J. Xin & R. Han, [Differentiation of B16 melanoma cells induced by ginsenoside RH2], Yao Hsueh Hsueh Pao 1996;31(10):742–5.
Abstract—Y. Kikuchi, et al., Inhibitors of human ovarian cancer cell proliferation in vitro by ginsenoside Rh2 and adjuvant effects to cisplatin in vivo, Anticancer Drugs Feb. 1991; 2(1):63–7.
Abstract—K.Y. Lee, et al., Ginsenoside–Rh2 blocks the cell cycle of SK–HEP–1 cells at the G1/S boundary by selectively inducing the protein expression of p27kip1, Cancer Lett. Dec. 20, 1996; 110(1–2):193–200.
Abstract—M. Oh, et al., Anti–proliferating effects of ginsenoside Rh2 on MCF–7 human breast cancer cells, Int. J. Oncol. May 1999; 14(5):869–75.
Abstract—T. Ota, et al., G1 phase–specific suppression of the Cdk2 activity by ginsenoside Rh2 in cultured murine cells, Life Sci. 1997; 60(2):PL39–44.
Abstract—H. Nakata, et al., Inhibitory effects of ginsenoside Rh2 on tumor growth in nude mice bearing human ovarian cancer cells, Jpn. J. Cancer Res. Jul. 1998; 89(7):733–40.
Abstract—H.E. Kim, et al., Ginsenoside RH–2 induces apoptotic cell death in rat C6 glioma via a reactive oxygen– and caspase–dependent but Bcl–X(L)–independent pathway, Life Sci. 1999; 65(3):PL33–40.
Abstract—J.A. Park, et al., Activation of caspase–3 protease via a Bcl–2–insensitive pathway during the process of ginsenoside Rh2–induced apoptosis, Canc. Lett. Dec. 16, 1997: 121(1):73–81.

(Continued)

Primary Examiner—Sabiha Qazi
(74) Attorney, Agent, or Firm—Synnestvedt & Lechner LLP

(57) ABSTRACT

This invention relates to a group of novel sapogenins, their use in anti-cancer applications, and to a process for their production. More particularly, this invention pertains to a novel group of dammarane sapogenins, PAM-120, PBM-110 and PBM-100 (the dammarance sapogenine structure is specifically clean of any sugar moieties (glycons) at any position and hydroxyl at C-20) and PAN-20 and PAN-30 (the dammarance sapogenin structure has sugar moieties but is free of hydroxyl at C-20), obtained by chemical cleavage of dammarane saponins. The invention also includes a novel application of the said sapogenins for anti-cancer treatment by using them separately or together, and/or jointly with other drugs, as well as to the process of producing these novel sapogenins. Said novel dammarane sapogenins show surprising anti-cancer effect when applied, particularly against multi-drug resistant cancers.

9 Claims, 4 Drawing Sheets

OTHER PUBLICATIONS

Abstract—K. Shinkai, et al., Inhibition of in vitro tumor cell invasion by ginsensoside Rg3, *Jpn. J. Cancer Res.* Apr. 1996 87(4):357–62.

Abstract—H. Iishi, et al., Inhibition by ginsenoside Rg3 of bombesin–enhanced peritoneal metastasis on intestinal adenocarcinomas induced by azoxymethane in Wistar rats, *Clin. Exp. Metastasis* Nov. 1997; 15(6):603–11.

Abstract—M. Mochizuki et a., Inhibitory effect of tumor metastasis in mice by saponins, ginsenoside–Rb2, 20(R)–and 20(S)–ginsenoside–Rg3, of red ginseng, *Biol. Pharm. Bull.* Sep. 1995; 18(9):1197–202.

Abstract—Lee, S.J., et al., Antitumor activity of a novel ginseng saponin metabolite in human pulmonary adenocarcinoma cells resistant to cisplatin, *Cancer Lett.* Sep. 20, 1999; 144(1):39–43.

Abstract—M. Yoshikawa, et al., Bioactive saponins and glycosides. XI. Structures of new dammarane–type triterpene oligoglycosides, quinquenosides I, II, III, IV, and V, from American ginseng, the roots of Panax quinquefolium L., *Chem. Phamr. Bull.* (Tokyo) Apr. 1998; 46(4):647–54.

Abstract—A.M. Popov, et al., [Comparative study of antitumor activity of the monoglucosides protopanaxadiol and betulafolientriol], *Antibiot. Khimioter.* Jul. 1994; 39(7):24–9.

Abstract—T. Kaku et al., Chemico–pharmacological studies on saponins of Panax ginseng C.A. Meyer. II. Pharmacological Part, *Arzneimittleforschung* Apr. 1975; 25(4):539–47.

Abstract—Y.S. Kim, et al., Ginsenoside Rh2 and Rh3 induce differentiation of HL–60 cells into granulocytes:modulation of protein kinase C isoforms during differentiation by ginsenoside Rh2, *Int. J. Biochem. Cell Biology* Mar. 1998;30(3):327–38.

Abstract—Y. Takino, [Studies on the pharmacodynamics of ginsenoside–Rg1, –Rb1 and –RB2 in rats], *Yakugaku Zasshi* Aug. 1994; 114(8):550–64. (Also list of titles of related articles.).

Abstract—N.M. Duc, et al., Saponins from Vietnamese ginseng, Panax vietnamensis Ha et Grushv. collected in central Vietnam. III. *Chem. Pharm. Bull.* (Tokyo) Mar. 1994;42(3):634–40.

Abstract—N.I. Baek, et a., Ginsenoside Rh4, a genuine dammarane glycoside from Korean red ginseng. *Planta Med.* Feb. 1996; 62(1):86–7.

Abstract—M. Yoshikawa, et al., Bioactive saponins and glycosides. VIII. Notoginseng (1): new dammarane–type triterpene oligoglycosides, notoginsensosides–A, –B, –C and –D, from the dried root of Panax notoginseng (Burk.) F.H. Chen. *Chem. Pharm. Bull.* (Tokyo) Jun. 1997;45(6):1039–45.

Abstract—D. Hou, et al., Separation and determination of chemical constituents in the volatile oil of three traditional Chinese crude drugs, *J. Pharm. Biomed. Anal.* Sep. 1998;17(8):1423–6.

Abstract—J.P. Hou, The chemical constituents of ginseng plants, *Comp. Med. East West* 1977 Summer;5(2):123–45.

Absract—J.F. Cui, et al., Gas chromatographic–mass spectrometric determination of 20(S)–protopanaxadiol and 20(S)–protopanaxatriol for study on human urinary excretion of ginsenosides after ingestion of ginseng preparations, *J. Chromatogr. B. Biomed. Sci. App.* Feb. 21, 1997; 689(2):349–55.

Abstract—J.F. Cui, et al., Analysis of ginsenosides by chromatography and mass spectrometry: release of 20 S–protopanaxadiol and 20 S–protopanaxatriol for quantitation, *Anal. Biochem.* May 1, 1993;210(2):411–7.

Absract—T. Ota, et al., Mechanism of action of ginsenoside Rh2: uptake and metabolism of ginsenoside Rh2 by cultured B16 melanoma cells, *J. Pharm. Sci.* Dec. 1991; 80(12):1141–6.

Abstract—C. Wakabayashi, et al., An intestinal bacerial metabolite of ginseng protopanaxadiol saponins has the ability to induce apoptosis in tumor cells, *Biochem. Biophys. Res. Commun.* May 29, 1998; 246(3):725–30.

Abstract—C. Wakabayashi, et al., In vivo antimetastic action of ginseng protopanaxadiol saponins is based on their intestinal bacterial metabolites after oral administration. *Oncol. Res.* 1997;9(8):411–7.

Abstract—S.J. Lee, et al., Antitumor activity of a novel ginseng saponin metabolite in human pulmonary adenocarcinoma cells resistant to cisplatin, *Cancer Lett.* Sep. 20, 1999; 144(1):39–43.

Abstract—H. Hasegawa & M. Uchiyama, Antimetastatic efficacy of orally administered ginsenoside Rb1 in dependence on intestinal bacterial hydrolyzing potential and significance of treatment with an active bacterial metabolite, *Planta Med.* Dec. 1998; 64(8):696–700.

Abstract—K. Okita, et al., Anti–growth effects with components of Sho–saiko–to (TJ–9) on cultured human hepatoma cells, *Eur. J. Cancer Prevention* 2(2):169–75, Mar. 1993.

Abstract—A.S. Attele, et al., Ginseng pharmacology: multiple constituents and multiple actions, *Biochemical Pharmacology,* 58(11):1685–93, Dec. 1, 1999.

Abstract—M. Oh, et al., Anti–proliferating effects of ginsenoside Rh2 on MCF–7 human breast cancer cells, *International Journal of Oncology,* 14(5):869–75, May 1999.

Abstract—J. Molnar, et al., Membrane associated antitumor effects of crocine–, ginsenoside– and cannabinoid derivatives, *Anticancer Research* 20(2A):861–7, Mar.–Apr. 2000.

Abstract—M. Mochizuki, et al., Inhibitory effect of tumor metastasis in mice by saponins, ginsenoside–Rb2, 20(R)– and 20(S)–ginsenoside–Rg3 of red ginseng, *Biological & Pharmaceutical Bulletin,* 18(9):1197–202, Sep. 1995.

www.rxlist.com/cgi/alt/ginseng.htm—article regarding ginseng.

online.daylight.com—print–outs showing chemical structures of panaxadiol, protopanaxadiol, protopanaxatriol, 20(R)–ginsenoside–h2, 20(S)–ginsenoside–Rh2, Dammara–20,24–dien–3beta–ol and Betalafolien(e)triol.

* cited by examiner

DAMMARANE SAPOGENINS, THEIR USE AS ANTI-CANCER AGENTS, AND A PROCESS FOR PRODUCING SAME

This is a continuation-in-part of application Ser. No. 09/910,887, filed Jul. 24, 2001.

FIELD OF THE INVENTION

This invention relates to novel dammarane sapogenins, their use in anti-cancer applications, and a process of producing the dammarane sapogenins. More particularly, the invention pertains to a novel group of dammarane sapogenins obtained by chemical cleavage of dammarane saponins extracted from panax ginseng, panax quinguefol, panax notoginseng and other species in the ginseng family, and a novel preparation of anticancer agent containing one or more of these novel sapogenins for the treatment of cancer, particularly multi-drug resistant cancers, as well as a process for producing these novel sapogenins.

BACKGROUND OF INVENTION AND RELATED ART

Since the beginning of the last decade, anti-cancer research has been increasingly directed to the discovery of novel anti-cancer agents obtained from natural sources, as well as identifying and preparing synthetic compounds found in natural sources.

Ginseng saponins (dammarane saponins, also called "ginsenosides", which are effective ingredients that organically exist in panax ginseng, panax quinguefol, panax notoginseng and other species in the ginseng family) and sapogenins (those that do not naturally exist in the ginseng plant or other species in the ginseng family and can be derived only through chemical structure modification by cleavage and/or semi-synthesis of dammarane saponins), as natural-source root compounds, have been broadly researched for their anti-cancer characteristics. Some of them have been reported to have anti-cancer effects, of which, for example, ginsenoside Rh2 [3-O-β-D-glucopyranosyl-20(s)-protopanaxadiol] has been reported for its anti-cancer activities [1], including induction of differentiation and apoptosis in cancer cells [5~11], inhibition of the growth of human ovarian cancer in nude mice after oral administration [9], and the ability to inhibit the multiplication of multi-drug resistance (MDR) cancer cells while used with other chemotherapy drugs in vitro [12].

Ginsenoside Rg3 [3-O-[β-D-glucopyranosyl(1→2)-β-D-glucopyranosyl]-20(s)-protopanaxadiol] has been reported to inhibit the invasion by various cancer cells [13] and suppress the proliferation of human prostate cancer cells [14] in vitro, and to inhibit lung metastasis in mice [15] and peritoneal metastasis in rats [16].

A metabolite of ginseng saponin produced by human intestinal bacteria, Mc [20-O-[α-L-arabinofuranosyl (1→6)-β-D-glucopyranosyl]-20(s)-protopanaxadiol], has been reported to inhibit the vascularization of tumors and extravasation of cancer cells [17].

While conventional chemotherapy agents directly attack the cancer cells and exhibit severe adverse side effects, some ginseng saponins and sapogenins, as well as their intestinal bacteria metabolites, have been reported to have inhibitory effects on cancers by induction of cancer-cell apoptosis and/or by suppression of vascularization of cancers with few adverse side effects.

In the case of treatment of cancers with ginseng saponins, it has been reported that saponins which are metabolized to sapogenins by intestinal bacteria have anti-cancer effects. It has also been reported that ginseng saponins with a hydroxyl at C-20(R), or 20(R) epimers, such as 20(R)-Rh2 and 20(R)-Rg3 have much lower biological activities than those with a hydroxyl at C-20(S), or 20(S) epimers, such as 20(S)-Rh2 and 20(S)-Rg3 respectively. Currently, mixtures of 20(R) and 20(S) epimers are very difficult if not impossible to separate. Thus the mixture has lower efficacy than that of 20(S) epimer. Furthermore, all previously discovered ginsenosides and sapogenins either have sugar moieties at C-3, C-6 or C-20, or have a hydroxyl at C-20, or have both.

SUMMARY OF THE INVENTION

This invention relates to a group of novel sapogenins, their use in anti-cancer applications, and to a process for their production. More particularly, this invention pertains to a novel group of dammarane sapogenins, PAM-20, PBM-110 and PBM-100 (the dammarane sapogenin structure in these three sapogenins is specifically clean of any sugar moieties (glycons) at any position and a hydroxyl at C-20) and PAN-20 and PAN-30 (the dammarane sapogenin structure has sugar moieties (glycons) but is free of hydroxyl at C-20), obtained by chemical cleavage of dammarane saponins. The invention also includes a novel application of the said sapogenins for anti-cancer treatment by using them separately or together, and/or jointly with other drugs, as well as to the process of producing these novel sapogenins. Said novel dammarane sapogenins show surprising anti-cancer effect when applied. In particular, the novel dammarane sapogenins show unexpected and superior activity against multi-drug resistant cancers.

The invention is directed to a sapogenin according to the formula:

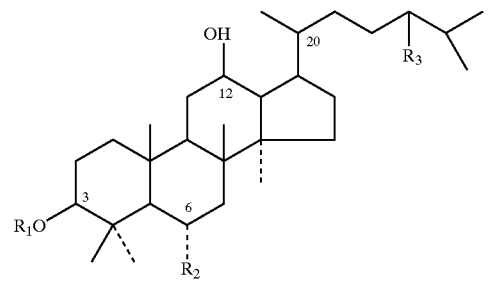

wherein R1 is H, glc or glc$^{1-2}$ glc, R2 is H or OH, R3 is H or OH; and when R1, R2 and R3 are H, there are double bonds at positions 20(21) and 24(25); and when R1 is H, R2 is OH and R3 is OH, there are double bonds at positions 20(22) and 25(26); and when R1 is H, R2 is OH and R3 is H, there are double bonds at positions 20(22) and 24(25); and when R1 is glc, R2 is H and R3 is H, there are double bonds at positions 20(21) and 24(25); and when R1 is glc$^{1-2}$glc, R2 is H and R3 is H, there are double bonds at positions 20(22) and 24(25); and pharmaceutically acceptable compositions incorporating said sapogenins.

The invention in one embodiment is directed to a sapogenin according to the formula:

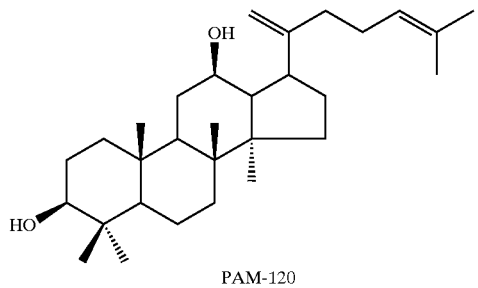

PAM-120

The invention in a second embodiment is directed to a sapogenin according to the formula:

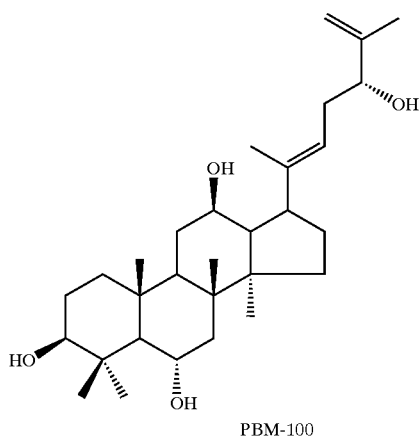

PBM-100

The invention in a third embodiment is directed to a sapogenin according to the formula:

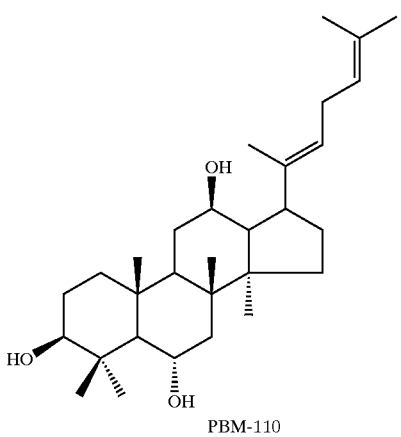

PBM-110

The invention in a fourth embodiment is directed to a sapogenin according to the formula:

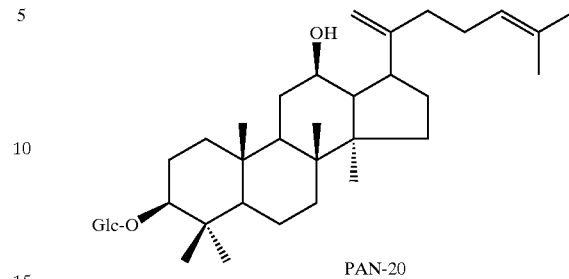

PAN-20

The invention is a fifth embodiment is directed to a sapogenin according to the formula:

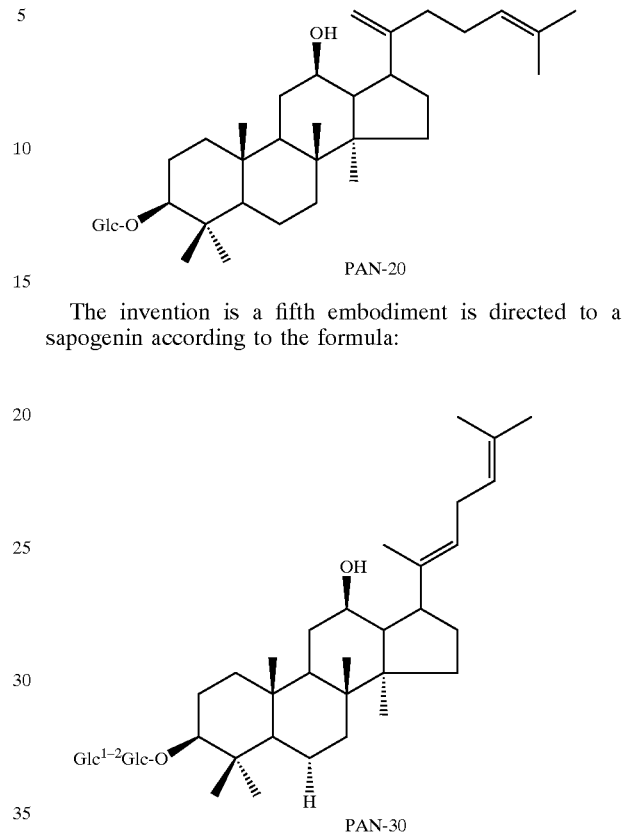

PAN-30

The invention also pertains to the use of a sapogenin according to the formula of the invention in treating cancer cells in a human being suffering from cancer, comprising killing cancer cells, inducing apoptosis in cancer cells, or inhibiting multiplication of cancer cells, or any combination thereof. The sapogenins of the invention are particularly useful in treating drug resistant cancer cells (MDR) in a human being suffering from cancer, comprising using the sapogenins either singly, or in combination with one another, or in combination with other chemotherapy agents.

The invention also pertains to a method of treating cancer in human beings or other animals suffering from cancer comprising administering to said human beings or other animals a therapeutically effective amount of a composition comprising one or more of PAM-120, PBM-100, PBM-110, PAN-20 and PAN-30.

The method can comprise a pharmaceutically effective amount of PAM-120, PBM-100, PBM-110, PAN 20 and PAN-30, with or without one or more pharmaceutically acceptable carriers. The active ingredient can be administered in a dosage of between 5 micrograms to 50 grams per 1 kg body weight per day. A preferred range is 50 micrograms to 5 grams per 1 kg body weight per day. The form of the composition can be selected from the group consisting of an orally administrable form, an injectable form, and a topically applicable form.

The orally administrable form can be selected from the group consisting of a tablet, a powder, a suspension, an emulsion, a capsule, a granule, a troche, a pill, a liquid, a spirit, a syrup and a lemonade. The injectable form can be selected from the group consisting of a liquid, a suspension and a solution. The topically applicable form can be selected from the group consisting of a drop, a paste, an ointment, a liquid, a powder, a plaster, a suppository, an aerosol, a liniment, a lotion, an enema and an emulsion. The composition can be administered to human beings or other animals who are receiving one or more other anti-cancer treatments. The composition can be formulated with one or more other anti-cancer agents, for additive treatment effects, or synergistic treatment effects on multidrug resistance cancers or any other cancer type.

The invention also includes the incorporation of the sapogenins according to the invention in foods, health foods, nutritional products, natural products and alternative medicine products.

The invention also pertains to a process of preparing a sapogenin which comprises producing a ginsenoside extract from plants selected from the group consisting of panax ginseng, panax quinguefol and panax notoginseng, and proceeding according to the following steps: (a) mixing the ginsenoside extract with water; (b) (i) mixing the ginsenoside extract and water with a short-chain (1–5 carbon) alkali-metal alcoholate solution or a hydroxide-ethanol solution to produce a mixture; and (ii) placing the resultant mixture in a reaction tank so that the resultant mixture can undergo chemical reactions under required high temperature and high pressure; or (c) (i) alternatively, mixing the ginsenosides extract with ethanol; (ii) mixing the extract and ethanol with alkali-metal alcoholates solution to produce a mixture, and (iii) placing the resultant mixture in a reaction tank so that the resultant mixture can undergo chemical reactions under required high temperature and high pressure; (d) after the reaction is completed, collecting an intermediate product of a mix of ginsenosides and sapogenins from the ethanol mixture; and (e) separating the desired sapogenins from the intermediate saponin-sapogenin mixture by silica-gel-column chromatography.

The alkali metal can be potassium or sodium. The hydroxide can be sodium hydroxide or potassium hydroxide. The alkali-metal alcoholates solution or the concentration of hydroxide-ethanol solution can be 5~50% (W/V). The alcohol can have 1–5 carbon atoms. The temperature of the reaction tank can be between 150~300° C. and the reaction pressure can be between 2.5~8.4 MPa. Preferably, the temperature is between 240–300° C. and the pressure is between 3.5~8.4 MPa.

DRAWINGS

In drawings which illustrate specific embodiments of the invention, but which should not be construed as restricting the spirit or scope of the invention in any way:

DETAILED DESCRIPTION OF THE INVENTION

Figure 1:
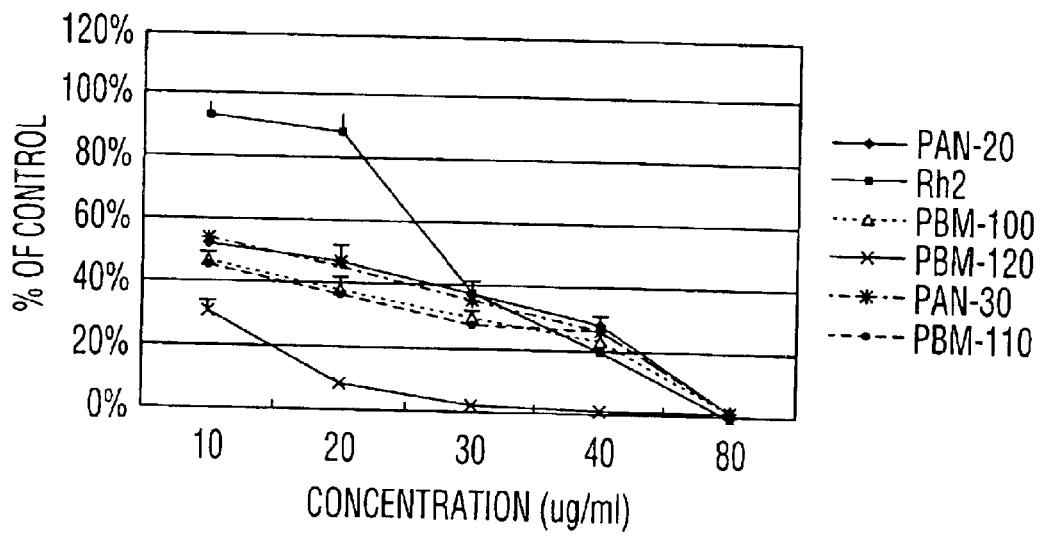
FIG. 1 illustrates a graph of tumor inhibiting effect of various ginsenosides on B16 cells.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention relates to a physically obtained group of novel compounds as follows:

Dammara-20(21)-diene-3,12-diol (named as PAM-120);

Dammara-20(22E)-diene-3,12,24-triol (named as PBM-100);

Dammara-20-(22E)-diene-3,6,12-triol (named as PBM-110);

3-O-β-D-glucopyranosyl-dammara-20(21)-diene-3,12-diol (named as PAN-20); and

3-O-[β-D-glucopyranosyl(1→2)-β-D-glucopyranosyl]-dammara-20(22E)-diene-3,12-diol (named as PAN-30).

The chemical formulas, structures and spectrum characteristics of the above listed novel compounds are shown on the following pages:

Sapogenin PAM-120
Dammara-20(21)-diene-3,12-diol (Named as PAM-120)

(1) Structural formula:

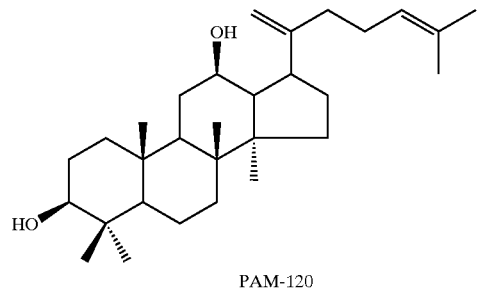

PAM-120

(2) Molecular formula: $C_{30}H_{50}O_2$
(3) Molecular weight: 442.723
(4) The $^1$H-NMR spectrum (300 MHz, $C_5D_5N$) has shown signals at $\delta 5.28$ (1H, br.t), $\delta 5.14$ (1H, s), $\delta 4.90$ (1H, s), $\delta 1.67$ (3H, s), $\delta 1.60$ (3H, s), $\delta 1.23$ (3H, s), $\delta 1.06$ (3H, s), $\delta 1.03$ (3H, s), $\delta 0.95$ (3H, s) and $\delta 0.90$ (3H, s).
(5) The $^{13}$C-NMR spectrum (75.4 MHz, $C_5D_5N$) has shown signals at $\delta 39.57$ (C-1), $\delta 28.31$ (C-2), $\delta 78.02$ (C-3), $\delta 40.30$ (C-4), $\delta 56.46$ (C-5), $\delta 18.84$ (C-6), $\delta 35.46$ (C-7), $\delta 37.53$ (C-8), $\delta 51.03$ (C-9), $\delta 39.61$ (C-10), $\delta 32.76$ (C-11), $\delta 72.51$ (C-12), $\delta 48.29$ (C-13), $\delta 51.27$ (C-14), $\delta 32.68$ (C-15), $\delta 27.12$ (C-16), $\delta 52.51$ (C-17), $\delta 15.91$ (C-18), $\delta 16.61$ (C-19), $\delta 155.57$ (C-20), $\delta 108.18$ (C-21), $\delta 33.91$ (C-22), $\delta 30.82$ (C-23), $\delta 125.38$ (C-24), $\delta 131.24$ (C-25), $\delta 25.81$ (C-26), $\delta 17.81$ (C-27), $\delta 28.73$ (C-28), $\delta 16.34$ (C-29) and $\delta 17.06$ (C-30).

Sapogenin PBM-100

Dammara-20(22E)-diene-3,12,24-triol (Named as PBM-100)

(1) Structural formula:

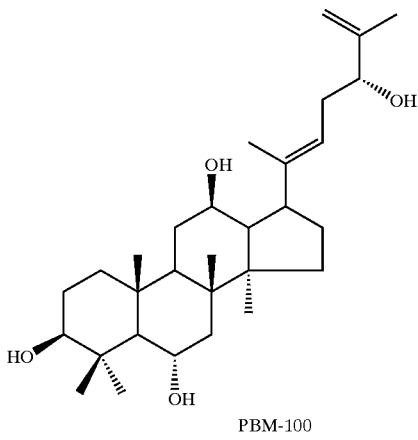

PBM-100

(2) Molecular formula: $C_{30}H_{50}O_4$
(3) Molecular weight: 474.721
(4) The $^1$H-NMR spectrum (300 MHz, $C_5D_5N$) has shown signals at δ5.31 (1H, br.t), δ5.22 (1H, s), δ4.82 (1H, s), δ1.95 (3H, s), δ1.81 (3H, s), δ1.66 (3H, s), δ1.64 (3H, s), δ1.47 (3H, s), δ1.19 (3H, s), δ1.06 (3H, s) and δ1.03 (3H, s).
(5) The $^{13}$C-NMR spectrum (75.4 MHz, $C_5D_5N$) has shown signals at δ39.48 (C-1), δ27.52 (C-2), δ78.48 (C-3), δ40.42 (C-4), δ61.86 (C-5), δ67.77 (C-6), δ47.69 (C-7), δ41.48 (C-8), δ50.55 (C-9), δ39.48 (C-10), δ32.02 (C-11), δ72.63 (C-12), δ50.47 (C-13), δ50.73 (C-14), δ32.69 (C-15), δ27.52 (C-16), δ50.92 (C-17), δ17.80 (C-18), δ17.70 (C-19), δ140.11 (C-20), δ13.23 (C-21), δ124.63 (C-22), δ30.04 (C-23), δ78.00 (C-24), δ149.90 (C-25), δ110.54 (C-26), δ17.80 (C-27), δ28.94 (C-28), δ16.56 (C-29) and δ17.14 (C-30).

Sapogenin PBM-110

Dammara-20(22E)-diene-3,6,12-triol (so named as PBM-110)

(1) Structural formula:

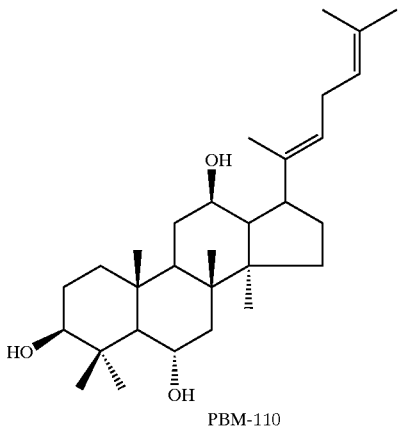

PBM-110

(2) Molecular formula: $C_{30}H_{50}O_3$
(3) Molecular weight: 458.722
(4) The $^1$H-NMR spectrum (300 MHz, $C_5D_5N$) has shown signals at δ5.31(1H, br.t), δ5.51 (1H, t, J=7.2 Hz), δ2.01 (3H, s), δ1.85 (3H, s), δ1.65 (3H, s), δ1.64 (3H, s), δ1.47 (3H, s), δ1.19 (3H, s), δ1.03 (3H, s) and δ1.01 (3H, s).
(5) The $^{13}$C-NMR spectrum (75.4 MHz, $C_5D_5N$) has shown signals at δ39.48 (C-1), δ27.52 (C-2), δ78.48 (C-3), δ40.42 (C-4), δ61.86 (C-5), δ67.77 (C-6), δ47.69 (C-7), δ41.48 (C-8), δ50.55 (C-9), δ39.48 (C-10), δ32.02 (C-11), δ72.63 (C-12), δ50.47 (C-13), δ50.73 (C-14), δ32.69 (C-15), δ27.52 (C-16), δ50.92 (C-17), δ17.80 (C-18), δ17.70 (C-19), δ140.11 (C-20), δ313.23 (C-21), δ124.63 (C-22), δ30.04 (C-23), δ124.63 (C-24), δ131.33 (C-25), δ25.76 (C-26), δ17.50 (C-27), δ28.94 (C-28), δ16.56 (C-29) and δ17.14 (C-30).

Sapogenin PAN-20

3-O-β-D-glucopyranosyl-dammara-20(21)-diene-3,12-diol (Named as PAN-20)

(1) Structural formula:

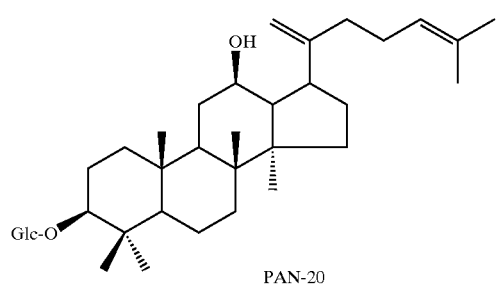

PAN-20

(2) Molecular formula: $C_{36}H_{60}O_7$
(3) Molecular weight: 604.863
(4) The $^1$H-NMR spectrum (300 MHz, $C_5D_5N$) has shown signals at δ4.92 (1H, d, J=7.5 Hz), δ5.29 (1H, br.t), δ5.14 (1H, s), δ4.90 (1H, s), δ1.66 (3H, s), δ1.60 (3H, s), δ1.30 (3H, s), δ1.02 (3H, s), δ0.98 (3H, s), δ0.98 (3H, s) and δ0.81 (3H, s).
(5) The $^{13}$C-NMR spectrum (75.4 MHz, $C_5D_5N$) for aglycon moiety has shown signals at δ39.34 (C-1), δ27.13 (C-2), δ88.82 (C-3), δ40.26 (C-4), δ56.47 (C-5), δ18.52 (C-6), δ35.40 (C-7), δ37.12 (C-8), δ50.91 (C-9), δ39.74 (C-10), δ32.73 (C-11), δ72.47 (C-12), δ48.30 (C-13), δ51.26 (C-14), δ32.74 (C-15), δ26.78 (C-16), δ52.52 (C-17), δ15.86 (C-18), δ16.52 (C-19), δ155.58 (C-20), δ108.19 (C-21), δ33.91 (C-22), δ30.82 (C-23), δ125.39 (C-24), δ131.25 (C-25), δ25.81 (C-26), δ17.81 (C-27), δ28.73 (C-28), δ16.83 (C-29) and δ17.05 (C-30). The $^{13}$C-NMR spectrum (75.4 MHz, C5D5N) for 3-glucopyranosyl has shown signals at δ107.00 (C-1"), δ75.82 (C-2"), δ78.79 (C-3"), δ71.94 (C-4"), δ78.39 (C-5") and δ63.14 (C-6").

Sapogenin PAN-30
3-O-[β-D-glucopyranosyl(1→2)-β-D-glucopyranosyl]-dammara-20(22E)-diene-3,12-diol (Named as PAN-30)

(1) Structural formula:

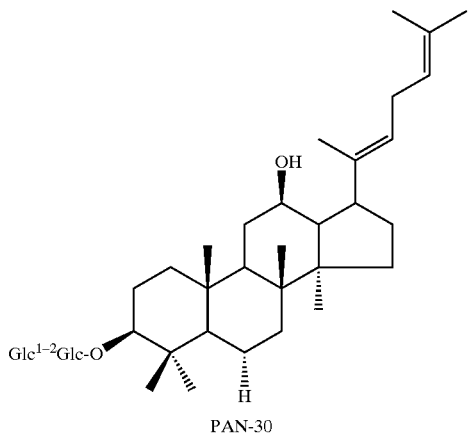

PAN-30

(2) Molecular formula: $C_{42}H_{70}O_{12}$
(3) Molecular weight: 766.587
(4) The $^{13}$C-NMR spectrum (75.4 MHz, C5D5N) has shown signals at δ39.17 (C-1), δ28.00 (C-2), δ88.82 (C-3), δ40.14 (C-4), δ56.29 (C-5), δ18.33 (C-6), δ35.24 (C-7), δ39.60 (C-8), δ50.66 (C-9), δ36.91 (C-10), δ32.10 (C-11), δ72.49 (C-12), δ50.33 (C-13), δ50.91 (C-14), δ32.54 (C-15), δ26.64 (C-16), δ50.80 (C-17), δ16.35 (C-18), δ16.49 (C-19), δ140.06 (C-20), δ13.07 (C-21), δ123.21 (C-22), δ27.35 (C-23), δ123.54 (C-24), δ131.16 (C-25), δ25.60 (C-26), δ17.66 (C-27), δ28.73 (C-28), δ15.72 (C-29) and δ16.92 (C-30).

The inventors herein have discovered that the dammarane sapogenin structure that is modified to be specifically clean of any sugar moieties (glycons) at any position and free of hydroxyl at C-20 has surprisingly improved effectiveness in treating cancers, particularly in treating multi-drug resistant cancers, compared to sapogenins that have sugar moieties on the structure or a hydroxyl at C-20 The inventors have unexpectedly found that PAM-120, PBM-110 and PBM-100, which all fall into this chemical category, have greater anti-cancer effect than other known saponins and sapogenins. In particular, these three sapogenins, and especially PAM-120, show surprisingly effective activity in the treatment of multi-drug resistant cancers.

The inventors have also surprisingly and unexpectedly found that a dammarane sapogenin structure which is free of a hydroxyl at C-20, even though there may be a sugar moiety on the structure, demonstrates effective anti-cancer activity, particularly in the treatment of multi-drug resistant cancers. PAN-20 and PAN-30, according to this invention, fall into this latter category.

While the inventors do not wish to be bound by any adverse theories if proved to be unfounded, the inventors offer the following as an aid in understanding the invention. It seems that sapogenins that have no hydroxyl at C-20 compared to sapogenins that have a hydroxyl at C-20 are surprisingly effective in cancer treatment. It also seems that a sapogenin that does not have a sugar moiety (glycon) on the sapogenin structure, is more effective than sapogenins that include a sugar moiety. It also seems that the diol is more effective than the triol. None of this could be predicted, or forecast without testing the sapogenins of the invention.

According to this invention and varying with the severity of symptoms experienced by the patient, the active daily dose of sapogenin PAM-120 is 0.1 mg—10 g per kg of body weight, or preferably, 1 mg—1 g per kg of body weight. The active daily dose of sapogenin PBM-110 is 0.1 mg—10 g per kg of body weight, or preferably, 1 mg—1 g per kg of body weight. The active daily dose of sapogenin PBM-100 is 0.1 mg—10 g per kg of body weight, or preferably, 1 mg—1 g per kg of body weight. The active daily dose of sapogenin PAN-20 is 0.1 mg—10 g per kg of body weight, or preferably, 1 mg—1 g per kg of body weight. The active daily dose of sapogenin PAN-30 is 0.1 mg—10 g per kg of body weight, or preferably, 1 mg—1 g per kg of body weight.

The anti-cancer agent according to this invention contains one or more of the said novel sapogenins PAM-120, PBM-100, PBM-110, PAN-20 and PAN-30, with or without other anti-cancer agent, used with or without one or more pharmaceutically acceptable carriers such as solid and liquid excipients.

The administration forms of the said anti-cancer agents according to the invention are listed as follows:

Injection forms, including but not limited to intramuscular (IM) injection, intravenous (IV) injection, subcutaneous injection and targeted-tissue injection in aqueous solutions, oil solutions, emulsion, or any forms;

Oral forms, including but not limited to tablets, capsules, granules, pills, suspensions, powders, sprits, emulsifiers, and syrups; and Topical form, including but not limited to drops, lotions, enemas, ointments, suspensions, paps, pastes, suppositories, aerosols, cataplasmas, emulsifiers, liniments, and plasters.

This invention also relates to a production process that can be used to commercially produce the above mentioned novel dammarane sapogenins for anti-cancer applications through chemical cleavage and semi-synthesis of dammarane saponins.

Figure 7:
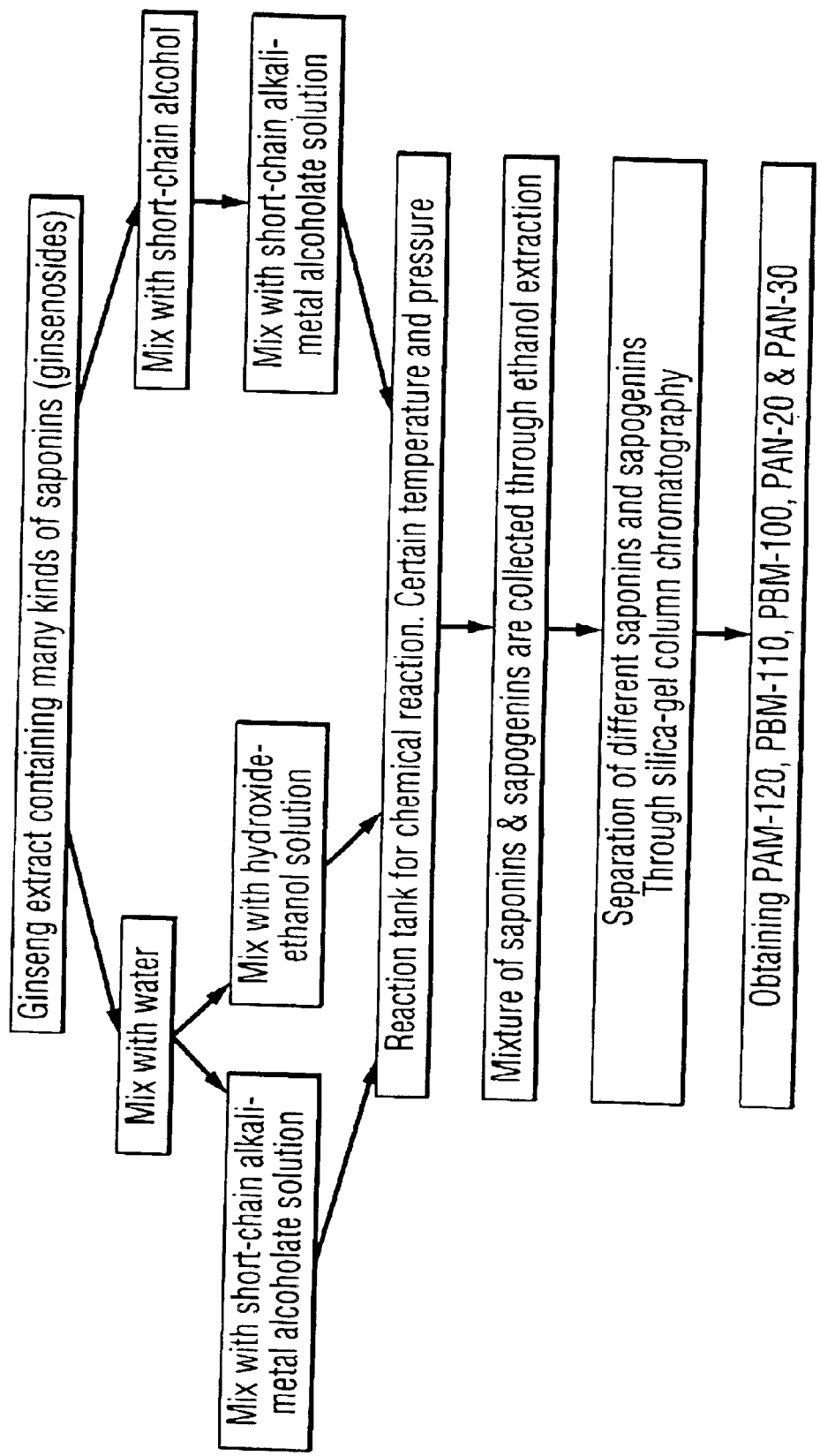
FIG. 7 illustrates a flow chart of two processes which can be used to obtain the sapogenins according to the invention.

FIG. 7 illustrates a flow sheet of two alternative processes which can be utilized to produce the sapogenins according to the invention. The production process according to the invention uses general ginsenosides (also called dammarane saponins including Ra, Rc, Rd. Re, etc.) extracted from plants selected from the ginseng family such as panax ginseng, panax quinguefol and panax notoginseng as raw materials. In the process, according to this invention, general ginsenosides are first mixed with water and then with short-chain (1–5 carbon) alkali-metal alcoholate solution or hydroxide-ethanol solution. The mixture is then put into a reaction tank to undergo chemical reactions under required high temperature and high pressure. Alternatively, general ginsenosides are first mixed with ethanol, and then with alkali-metal alcoholates solution. The mixture is thereafter put into a reaction tank to undergo chemical reactions under required high temperature and high pressure. After the required period of time for the reaction to be complete, the intermediate product of a mix of ginsenosides and sapogenins are collected from the ethanol solution. The next step is to separate the desired dammarane sapogenins from the intermediate saponin-sapogenin mix by using silica-gel-column chromatography. According to this invention, the said alkali metal can be potassium or sodium, the hydroxide can be sodium hydroxide or potassium hydroxide, the concentration of alkali-metal alcoholates solution or the concentration of hydroxide-ethanol solution can be 5~50% (W/V), and the short chain alcohol can be one with 1~5 carbon atoms. In this invention, during the production process, the reaction tank's temperature can be between 150~300° C. and the reaction pressure is between 2.5~8.4 MPa. Preferably, the reaction temperature is between about 240~300° C. and the reaction pressure is between about 3.5–8.4 MPa.

Cancers susceptible to treatment with the compounds of the invention alone or in combination with a chemotherapeutic in accordance with various aspects of the invention may include both primary and metastatic tumors and hyperplasias, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choricarcinoma and gestational trophoblastic disease)), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), and tumors of the brain, nerves, eyes, and meninges (including astrocytomas, gliomas, glioblastomas, retinoblastomas, neuromas, neuroblastomas, Schwannomas, and meningiomas). In some aspects of the invention, the compounds of the invention in combination with a chemotherapeutic may also be useful in treating hematopoietic cancers such as leukemias (i.e. chloromas, plasmacytomas and the plaques and tumors of mycosis fungoides and cutaneous T-cell lymphoma/leukemia) and lymphomas (both Hodgkin's and non-Hodgkin's lymphomas).

The compounds of the invention and the chemotherapeutic may be administered in combination separately or as one single combined pharmaceutical composition. The amount of each component administered may be determined by an attending clinician, taking into consideration a variety of factors such as the etiology and severity of the disease, the patient's condition and age and the potency of each component. the components may be administered in accordance with the standard methodologies as, for example, disclosed in the Physician's Desk Reference (PDR) published by Medical Economics Co. Inc. of Oradell, N.J.

One or more pharmaceutically acceptable carriers or excipients may be used to formulate pharmaceutical compositions of the invention, including solvents, dispersion media, coatings, antibacterial and antifungal agents, isotonic and absorption delaying agents, and the like that are physiologically compatible. In alternative embodiments, the carrier may be suitable for parenteral, intravenous, intraperitoneal, intramuscular, sublingual or oral administration. Pharmaceutically acceptable carriers may include sterile aqueous solutions or dispersions and sterile powders for the extemporaneous preparation of sterile injectable solutions or dispersion. Except insofar as any conventional media or agent is incompatible with the active compound, use thereof in the pharmaceutical compositions of the invention is contemplated. Supplementary active compounds can also be incorporated into the pharmaceutical compositions.

Pharmaceutical compositions typically must be sterile and stable under the conditions of manufacture and storage. The composition may be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about the including in the composition an agent which delays absorption, for example, monostearate salts and gelatin. Moreover, the pharmaceutical compositions may be administered in a time release formulation, for example, in a composition which includes a slow release polymer. The active compounds can be prepared with carriers that will protect the compound against rapid release, such as controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating an active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof. Pharmaceutical compositions may be formulated with one or more compounds that enhance the solubility of the active compounds.

EXAMPLES

Examples of Preparation Processes

Example 1

Preparation Process of Producing PAM-120, PBM-100, and PAN-20

[1] Ginseng crude extract 10 g was dissolved in 40 mL of 95% ethanol

[2] Add 40 mL of 5 N NaOH

[3] Pour into the reaction tank, and set temperature to 240° C., and pressure to 3.5 Mpa, for 1.5 hours

[4] Reduce temperature to room temperature, and take the products out the tank

[5] Add HCl to neutralize pH to about 7, and expend the volume to 800 mL using water

[6] Extract 3 times with acetic ester, 100 mL each time

[7] Combine all the extracts, and reduce the pressure to dry. Thus, obtain 3.8 g of dried extracts

[8] Grind and dissolved the extract in 20 mL of methanol, and mix the methanol solution with silica gel

[9] Dry up the mixture, and then grind to fine powder

[10] Load the Silica gel column

[11] Wash the column with 60 mL of ether:petroleum benzin (1:3), and thus, 250 mg of PAM-120, and 45 mg of PBM-100 were obtained Wash the column with 90 mL of chloroform:methanol (95:5), and thus 50 mg of PAN-20 was obtained.

Example 2

Another Example of Preparation Process Producing PAM-120, PBM-100, and PAN-20

[1] 10 g of Ginseng crude extract was added into reaction tank
[2] Add to the reaction tank 100 mL of 5 N NaOH
[3] Set temperature to 270° C. and pressure to 4.5 Mpa for 1 hour
[4] Reduce temperature to room temperature, then take out the products
[5] Neutralize the pH to 7 using HCl
[6] Filter and keep the solids
[7] Dissolve the solids in 10 mL of 95% Ethanol
[8] Add water to make ethanol content less than 5%
[9] Sit still overnight
[10] Filter and keep the solids
[11] Dry the solids
[12] Dissolved the solids in 10 mL of methanol
[13] Filter and keep the solution
[14] Dry the solution to obtain 3.6 g of products
[15] Mix the products with 11 g of silica gel
[16] Grind and then load the silica gel column
[17] Wash the column with 100 mL of ether:petroleum benzin (1:3), and thus, 60 mg of PAM-120, and 65 mg of PBM-100 were obtained.
[18] Wash the column with chloroform:methanol (95:5), and thus 60 mg of PAN-20 was obtained.

Example 3

Comparison of Cancer Cell Inhibition Effects in vitro Between Ginsenoside 20(S)-Rh2 and Novel Dammarane Sapogenins PAM-120, PBM-100, PAN-30 and their Composition A. Method Composition: 20(S)-Rh2 was provided by Shenyang Pegasus Pharmaceutical R&D Co., China, with a purity of over 98%. The molecular weight for Rh2 was 622.3. Sapogenins PAM-120, PBM-100 and PAN-30 were derived from the process stated in Example 1. The molecular weights of PAM-120, PBM-100 and PAN-30 were respectively 442.7, 474.7 and 766.6, and the purity for each of the three agents was higher than 99%. Rh2, PAM-120, PBM-100 and PAN-30 were dissolved 1 gram each separately in 100 ml absolute ethanol and stored at 4° C. the agents were diluted with RPMI-1640 medium to the desired concentrations as shown in Table 1.

Cells: Human non-small-cell lung carcinoma H460 cells were incubated in RPMI-1640 medium added with 10% fetal calf serum, 100 units penicillin/ml, and 100 µg streptomycin/ml in 5% $CO_2$ at 37° C.

In vitro treatment: H460 cells were seeded in 96-well flat-bottomed microtest-plates at $1.2 \times 10^3$ cells per well, six wells in each group, incubated in humidified 5% $CO_2$ at 37° C. for 24 hours with or without the agents according to the schedule as shown below.

TABLE 1

| Group | DOSAGE | Dosage (µg/ml) |
|---|---|---|
| Control | No drug | — |
| Low-dose | Rh2 | 25 |
|  | PAM-120 |  |
|  | PBM-100 |  |
|  | PAN-30 |  |
| High-dose | Rh2 | 40 |
|  | PAM-120 |  |
|  | PBM-100 |  |
|  | PAN-30 |  |

After the 24 hours of incubation, an equal volume of 10% formalin phosphate-buffered saline containing 0.2% crystal violet was added to each well and left at room temperature for 20 minutes. The plates were then washed twice with distilled water and dried at room temperature. The absorbency of the stained cells at 590 nm was then measured using an automatic microtest-plate reader. Average absorbency of the control wells ($A_c$) without any treatment was calculated, average absorbency of each treatment group ($A_{Ti}$) was determined, and then the average cell viability of each treatment group ($V_i$) was derived using the following formula:

$$V_i (\%) = \frac{A_{Ti}}{A_c} \times 100\%$$

B. Result

TABLE 2

| Group | | Absorbency of Stained Cells (M ± SD) | V(%) | tTest w/ Control | tTest w/ Rh2 |
|---|---|---|---|---|---|
| Control | No drugs | .368 ± .069 | 100.00 | | |
| Low-dose (25 µg/ml) | Rh2 | .278 ± .030 | 78.49 | P < 0.01 | |
|  | PAM-120 | .220 ± .051 | 62.08 | P < 0.01 | P < 0.05 |
|  | PBM-100 | .223 ± .040 | 62.72 | P < 0.01 | P < 0.05 |
|  | PAN-30 | .249 ± .045 | 70.30 | P < 0.01 | |
| High-dose (40 µg/ml) | Rh2 | .181 ± .049 | 50.99 | P < 0.01 | |
|  | PAM-120 | .125 ± .031 | 35.34 | P < 0.01 | P < 0.05 |
|  | PBM-100 | .130 ± .019 | 36.51 | P < 0.01 | P < 0.05 |
|  | PAN-30 | .147 ± .032 | 41.49 | P < 0.01 | |

The results in Table 2 show a significant inhibitory effect on proliferation of H460 cells by each of the novel compounds PAM-120, PBM-100 and PAN-30 (P<0.01 compared with that of the Rh2 control), and a notable increase in inhibitory effect of PAM-120 and PBM-100 on the proliferation of H460 cells (P<0.05 compared with that of Rh2).

Example 4

Tumor Weight Test

A. Method

Forty (40) C57BL/6J mice weighing 18–22 g were randomly divided into four groups: one control group and three treatment groups, each with 10 animals. Mouse sarcoma 180 cells were hyperdermically transplanted into the mice by using a transplantation needle under the right armpit. After the transplantation, all mice formed a tumor. The mix composition of ginsenosides and sapogenins including the three novel dammarane sapogenins (PAM-120, PBM-100 and PAN-30), derived as an intermediate product from the process described in Example 2, was prepared into a suspension form. The mice were weighed daily prior to drug administration to determine the actual measurement of drug administered. The drug administration started from 24 hours post tumor transplantation. The mice in the three treatment groups were orally given the mix composition at a daily dose of 0.4 mg/kg, 1.2 mg/kg and 3.6 mg/kg respectively for 8 days using a gastric catheter. The mice in the control group were orally given a normal saline placebo. 24 hours after the last administration of the drug, the mice were sacrificed with an overdose of anesthetics. The weight of the sarcoma in each mouse was measured. The average tumor weight of each treatment group ($Wt_i$) and that of the control group (Wc) were calculated, and the tumor inhibition ratio ($R_i$) of each treatment group was determined with the following formula:

$$R_i (\%) = \frac{Wc - Wt_i}{W_c} \times 100\%$$

B. Result

TABLE 3

TUMOR WEIGHT RATIO (%)

| GROUP | MICE# | Tumor Weight (g) (M ∓ SD) | R(%) | P |
|---|---|---|---|---|
| Control | 10 | 2.995 ∓ 0.621 | | |
| Mix 0.4 mg/kg | 10 | 1.269 ∓ 0.525 | 57.63 | <0.01 |
| Mix 1.2 mg/kg | 10 | 0.725 ∓ 0.270 | 75.79 | <0.01 |
| Mix 3.6 mg/kg | 10 | 0.388 ∓ 0.130 | 87.04 | <0.01 |

The results in Table 3 have demonstrated that oral administration of the subject mix composition, the intermediate product from Example 2, achieves tumor inhibition ratios of 58%, 76% and 87% respectively at the doses of 0.4 mg/kg, 1.2 mg/kg and 3.6 mg/kg, showing a dose related anti-cancer efficacy of the mix of the intermediate product of Example 2 containing the three novel sapogenins PAM-120, PBM-100 and PAN-30 and some other saponins and sapogenins whose structures are known or unknown.

Example 5

Cancer Bearing Mice Life Prolongation Test

A. Method

Fifty (50) C57BL/6J mice weighing 18–22 g, without sex discrimination, were randomly assigned to one control group and four treatment groups, each with 10 animals. Murine sarcoma 180 cells were intraperitoneally transplanted to the mice. 20(S)-Rh2 was provided by Shenyang Pegasus Pharmaceutical R&D Co., China, with a purity of over 98%. The molecular weight for Rh2 was 622.3. The novel sapogenin PAM-120 was derived from the process described in Example 2 according to this invention. The molecular weight of PAM-120 was 442.7, and the purity for PAM-120 was higher than 99%. The drugs were prepared into a suspension form respectively. The mice were weighed daily prior to drug administration to determine the actual measurement of drug administered. Drug administration started from 24 hours post tumor inoculation. The mice in the two low-dose treatment groups were orally given the Rh2 and PAM-120 preparations using a gastric catheter at a daily dose of 10 mg/kg of Rh2 and 10 mg/kg of PAM-120 respectively for a lifetime or up to 120 days. The mice in the two high-dose treatment groups were orally given the Rh2 and PAM-120 preparations using a gastric catheter at a daily dose of 25 mg/kg of Rh2 and 25 mg/kg of PAM-120 respectively for a lifetime or up to 120 days. The mice in the control group were orally given a normal saline. For each group, the days of survival for 50% animals ($DS_{50}$) and the average days of survival (ADS) were recorded. For groups containing one or more animals that could have lived longer than 120 days (the designed sacrifice day was d 120), the ADS would be so calculated that these animals were counted as if they had died on day 120, and a note would be made. The life prolongation rate (LPR) was calculated with the following formula:

$$LPR (\%) = \frac{ADS_{(treatment)} - ADS_{(control)}}{ADS_{(control)}} \times 100\%$$

B. Result

TABLE 4

MURINE SARCOMA 180 BEARING MICE LIFE PROLONGATION RATE

| | | % | |
|---|---|---|---|
| Group | $DS_{50}$ | ADS(M ∓ SD) | LPR(%) |
| Control | 14 | 14.7 ∓ 5.4 | |
| Rh2 (10 mg/kg) | 22 | 24.7 ∓ 12.6 | 68.0 |
| PAM-120 (10 mg/kg) | 38 | 38.6 ∓ 16.4 | 162.6 |
| Rh2 (25 mg/kg) | 41 | 44.3 ∓ 19.6 | 201.4 |
| PAM-120 (25 mg/kg) | 77 | 80.6 ∓ 34.4 | 448.3 |

The anti-cancer effect of the novel sapogenin PAM-120 was indicated by the significant increase in life prolongation of the mice bearing murine sarcoma (P<0.01 compared with the average days of survival in the control). Better anti-cancer effect of novel sapogenin PAM-120 on murine sarcoma than that of Rh2 was demonstraated by the significant increase in life prolongation of the sarcoma-bearing mice (P<0.01, compared with the average days of survival in the relevant Rh2 treatment dose groups). Two mice in the 25 mg/kg composition treatment group survived for the whole 120 days, and were found to have no tumors whatsoever existing in their bodies postmortally.

FIG. 1 illustrates a graph of tumor inhibiting effect of various ginsenosides on B16 cells. Mouse melanoma tumor B16 cells were cultured with DMEM and 5% serum supplement in 96-well dishes. Cells were then treated with various concentrations of PAN-20, PAN-30, PBM-100, PBM-110, PAM-120 and Rh2, respectively. The number of alive cells were measured using MTT method 24 hours after the treatment and compared with the control samples. All the new compounds showed a significantly higher tumor inhibitory effect than RH2, especially at low concentrations (p<0.01, Student t test).

Figure 2:
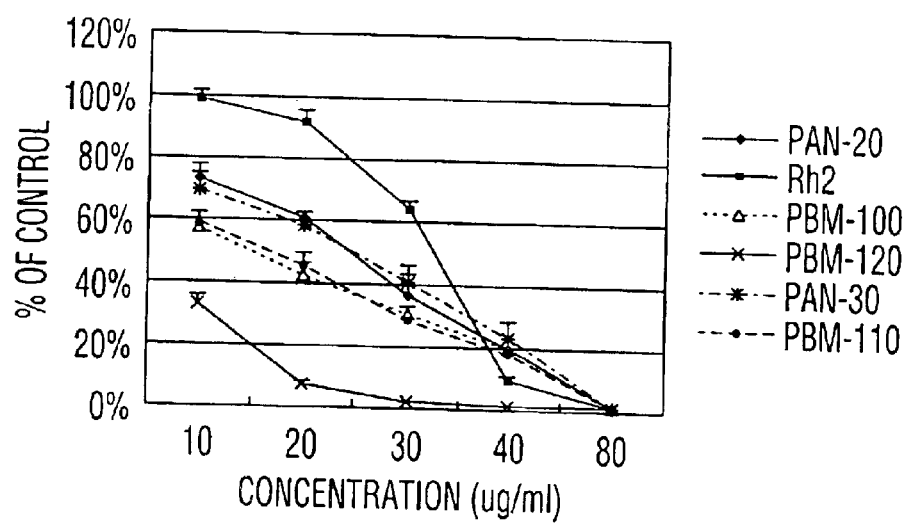
FIG. 2 illustrates a graph of tumor inhibiting effect of various ginsenosides on drug resistant human breast cancer cells MCF7r.

FIG. 2 illustrates a graph of tumor inhibiting effect of various ginsenosides on drug resistant human breast cancer cells MCF7r. Human drug resistant breast cancer cells (MCF7r) were cultured with DMEM and 5% serum supplement in 96-well dishes. Cells were then treated with various concentrations of PAN-30, PBM-100, PBM-110, PBM-120, and Rh2, respectively. The number of alive cells were measured using MTT method 24 hours after the treatment and compared with the control samples. All new compounds showed a significantly higher tumor inhibitory effect than Rh2, especially at low concentrations (p<0.01, Student t test).

Figure 3:
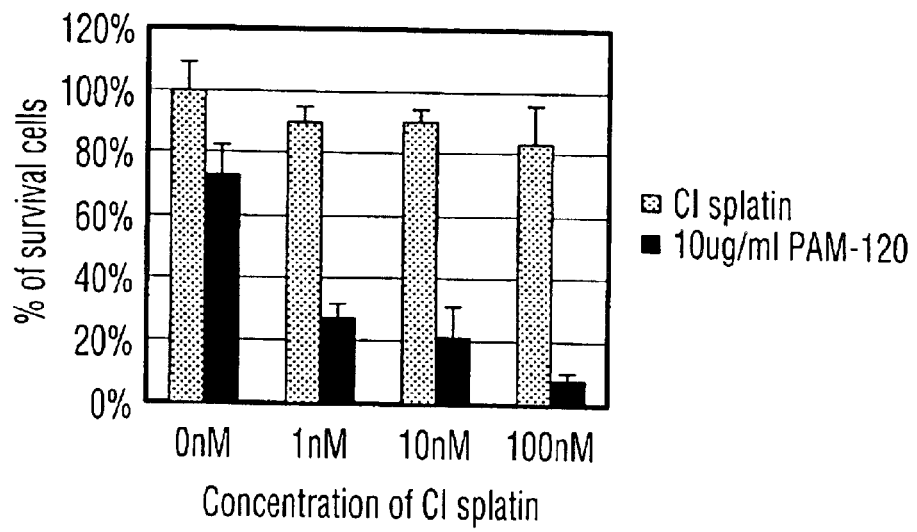
FIG. 3 illustrates a plot of the synergistic effect of PAM-120 with cisplatin on drug resistant human breast cancer cells MCF7r.

FIG. 3 illustrates a plot of the synergistic effect of PAM-120 with Cisplatin on drug resistant human breast cancer cells MCF7r. MCF7r cells were treated with anti-cancer chemotherapy agent Cisplatin at various concentrations in the presence of 10 ug/ml PAM-120. In FIG. 3, the first bars in each concentration group represent percentages of alive cells 24 hours after treatment with Cisplatin only. The second bars in each group represent the results of cells treated with Cisplatin and PAM-120.

Figure 4:
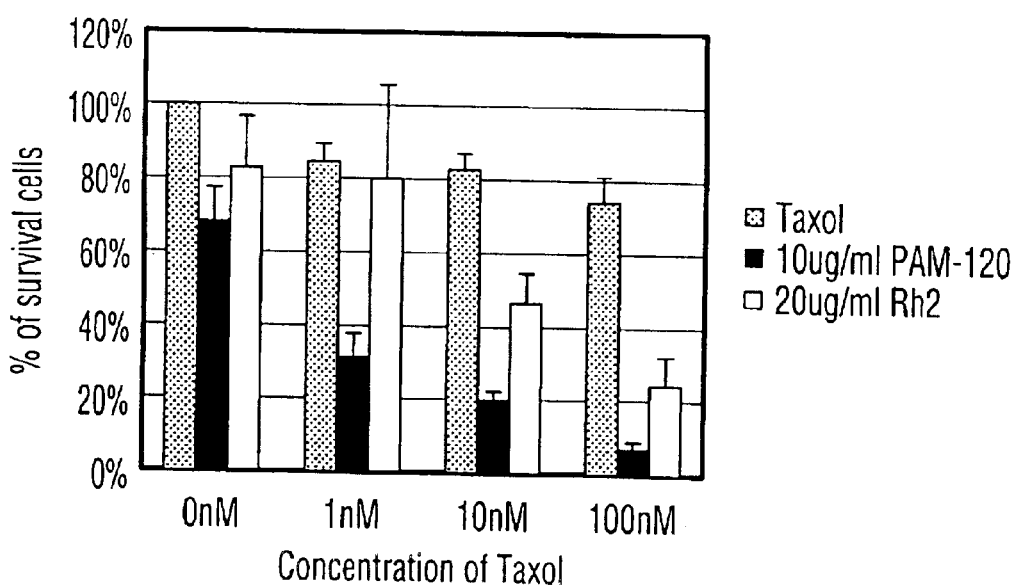
FIG. 4 illustrates a plot of the synergistic effect of PAM-120 with taxol on drug resistant human breast cancer cells MCF7r.

FIG. 4 illustrates a plot of the synergistic effect of PAM-120 with Taxol on drug resistant human breast cancer cells MCF7r. MCF7r cells were treated with anti-cancer chemotherapy agent Taxol at various concentrations in the presence of 10 ug/ml PAM-120 or 20 ug/ml RH2. In FIG. 4, the first bars in each concentration group represent percentages of alive cells 24 hours after treatment with Taxol only. The second bars in each group represent the results of cells treated with Taxol and PAM-120, while the third bars represent the results of cells treated with 20 ug/ml Rh2.

Figure 5:
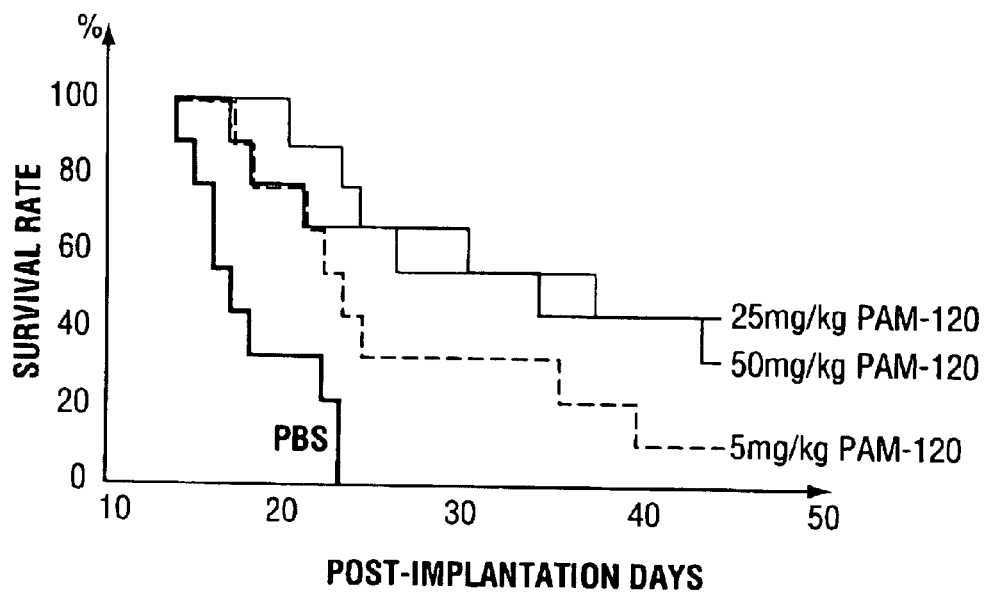
FIG. 5 illustrates a graph of the therapeutic effect of PAM-120 on mouse intracranial human malignant glioma (U87) model.

FIG. 5 illustrates a graph of the therapeutic effect of PAM-120 on mouse intracranial human malignant glioma (U87) model. Nude mice were intracranially implanted with human malignant glioma cells (U87). On day 10 post tumor implantation, animals were treated with various dosages of PAM-120. Animals treated with 25 mg/kg and 50 mg/kg PAM-120 had significantly longer survival time after tumor implantation (p<0.01, Kaplan Meier analysis).

Figure 6:
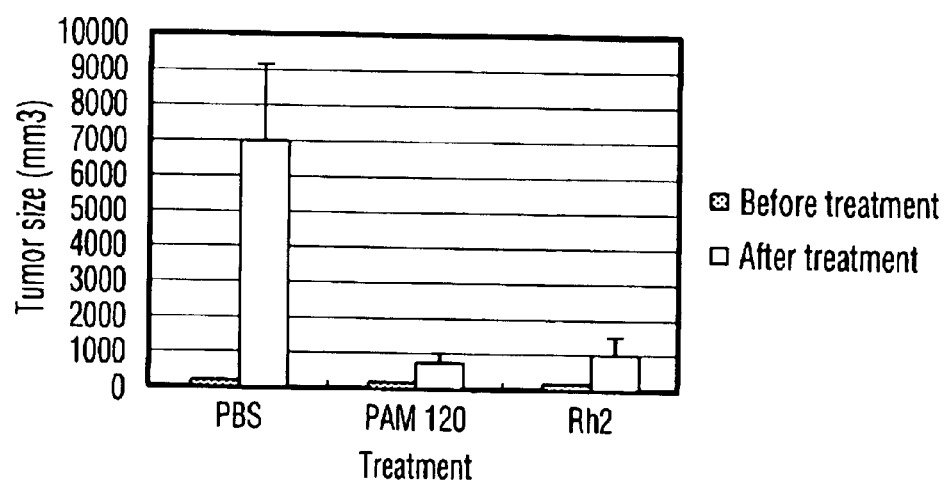
FIG. 6 illustrates a graph of the therapeutic effect of PAM-120 on mouse subcutaneous human malignant glioma (U87) model.

FIG. 6 illustrates a graph of the therapeutic effect of PAM-120 on mouse subcutaneous human malignant glioma (U87) model. Nude mice were subcutaneously implanted with human malignant glioma cells (U87). On day 7 post tumor implantation, animals were treated with 25 mg/ml PAM-120 or equal dose of Rh2. Tumor sizes were measured on day 7 (before treatment) and day 24 (after the treatment). Both PAM-120 and Rh2 significantly inhibited tumor growth comparing to PBS control animals. Tumor sizes in PAM-120 treated animals were significantly smaller than those in the Rh2 treated animals (p<0.05).

FIG. 7 illustrates a flow chart of two processes which can be used to obtain the sapogenins according to the invention.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

CITED REFERENCES

1. Kim N D, Park M K, Lee S K, Park J H, Kim J M (1998) Processed ginseng product with enhanced pharmacological effects. U.S. Pat. No. 5,776,860.
2. Lee Y N, Lee H Y, Chung H Y, Kim S I, Lee S K, Park B C, Kim K W (1996) In vitro induction of differentiation by ginsenosides in F9 teratocarcinoma cells. Eur J Cancer. 1420–8
3. Odashima S, Ohta T, Kohno H, Matsuda T, Kitagawa I, Abe H, Arichi S (1985) Control of phenotypic expression of cultured B16 melanoma cells by plant glycosides. Cancer Res. 85: 2781–8
4. Xia L J, Han R (1996) [Differentiation of B16 melanoma cells induced by ginsenoside RH2]. Yao Hsueh Hsueh Pao. 31: 782–5
5. Kikuchi Y, Sasa H, Kita T, Hirata J, Tode T, Nagata I (1991) Inhibition of human ovarian cancer cell proliferation in vitro by ginsenoside Rh2 and adjuvant effects to cisplatin in vivo. Anti-cancer Drugs. 2: 63–7
6. Lee K Y, Park J A, Chung E, Lee Y H, Kim S I, Lee S K (1996) Ginsenoside-Rh2 blocks the cell cycle of SK-HEP-1 cells at the G1/S boundary by selectively inducing the protein expression of p27kip1. Cancer Lett. 110: 193–200
7. Oh M, Choi Y H, Choi S, Chung H, Kim K, Kim S I, Kim D K, Kim N D (1999) Anti-proliferating effects of ginsenoside Rh2 on MCF-7 human breast cancer cells. Int J Oncol. 18: 869–75
8. Ota T, Maeda M, Odashima S, Ninomiya T J, Tatsuka M (1997) G1 phase-specific suppression of the Cdk2 activity by ginsenoside Rh2 in cultured murine cells. Life Sci. 60: PL39–88
9. Nakata H, Kikuchi Y, Tode T, Hirata J, Kita T, Ishii K, Kudoh K, Nagata I, Shinomiya N (1998) Inhibitory effects of ginsenoside Rh2 on tumor growth in nude mice bearing human ovarian cancer cells. Jpn J Cancer Res. 89: 733–80
10. Kim H E, Oh J H, Lee S K, Oh Y J (1999) Ginsenoside RH-2 induces apoptotic cell death in rat C6 glioma via a reactive oxygen- and caspase-dependent but Bcl-X(L)-independent pathway. Life Sci. 65: PL33–80
11. Park J A, Lee K Y, Oh Y J, Kim K W, Lee S K (1997) Activation of caspase-3 protease via a Bcl-2-insensitive pathway during the process of ginsenoside Rh2-induced apoptosis. Cancer Lett. 121: 73–81
12. Jia W (2000) Ginsenoside Chemotherapy. U.S. Patent Provisional File—Serial No. 60/204/765
13. Shinkai K, Akedo H, Mukai M, Imamura F, Isoai A, Kobayashi M, Kitagawa I (1996) Inhibition of in vitro tumor cell invasion by ginsenoside Rg3. Jpn J Cancer Res. 87: 357–62.
14. Liu W K, Xu S X, Che C T (2000) Anti-proliferative effect of ginseng saponins on human prostate cancer cell line. Life Sci. 67(11):1297–306.
15. Iishi H, Tatsuta M, Baba M, Uehara H, Nakaizumi A, Shinkai K, Akedo H, Funai H, Ishiguro S, Kitagawa I (1997) Inhibition by ginsenoside Rg3 of bombesin-enhanced peritoneal metastasis of intestinal adenocarcinomas induced by azoxymethane in Wistar rats. Clin Exp Metastasis 15: 603–11.
16. Mochizuki M, Yoo Y C, Matsuzawa K, Sato K, Saiki I, Tono-oka S, Samukawa K, Azuma I (1995) Inhibitory effect of tumor metastasis in mice by saponins, ginsenoside-Rb2, 20(R)- and 20(S)-ginsenoside-Rg3, of red ginseng. Biol Pharm Bull. 18: 1197–202.
17. Hasegawa H, Jong H S, Matsumiya S, Uchiyama M, Jae D H (1999) Metabolites of Ginseng Saponins by Human Intestinal Bacteria and Its Preparation for an Anti-cancer. U.S. Pat. No. 5,919,770.

What is claimed is:

1. A process of preparing a sapogenin according to the formula:

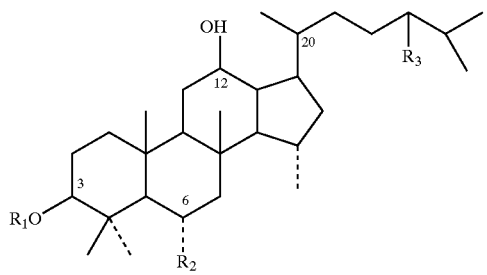

wherein $R_1$ is H or glc, $R_2$ is H or OH, $R_3$ is H or OH; and when $R_1$, $R_2$, and $R_3$ are H, there are double bonds at positions 20(21) and 24(25); and when $R_1$ is H, $R_2$, is OH and $R_3$ is OH, there are double bonds at positions 20(22) and 25(26); and when $R_1$ is glc, $R_2$ is H and $R_3$ is H, there are double bonds at positions 20(21) and 24(25); which process comprises:

producing a ginsenoside extract from plants selected from the group consisting of panax ginseng, panax quinguefol and panax notoginseng, or a sapogenin source from some other plant, and proceeding according to the following steps:
(a) mixing the ginsenoside extract with water;
(b) (i) mixing the ginsenoside extract and water with a short-chain (1–5 carbon) alkali-metal alcoholate solution or a hydroxide-ethanol solution to produce a mixture; and
  (ii) placing the resultant mixture in a reaction tank so that the resultant mixture can undergo chemical reactions under high temperature and high pressure effective to produce sapogenins therefrom; or
(c) (i) alternatively, mixing the ginsenosides extract with ethanol;
  (ii) mixing the extract and ethanol with alkali-metal alcoholates solution to produce a mixture, and
  (iii) placing the resultant mixture in a reaction tank so that the resultant mixture can undergo chemical reactions under high temperature and high pressure effective to produce sapogenins therefrom;
(d) after the reaction is completed, collecting an intermediate product of a mix of gensenosides and sapogenins from the ethanol mixture; and
(e) separating the desired sapogenins from the intermediate saponin-sapogenin mixture by silica-gel-column chromatography.

2. A process as claimed in claim 1 wherein the alkali metal can be potassium or sodium.

3. A process as claimed in claim 1 wherein the hydroxide can be sodium hydroxide or potassium hydroxide.

4. A process as claimed in claim 1 wherein the alkali-metal alcoholates solution or the concentration of hydroxide-ethanol solution is 5~50% (W/V).

5. A process as claimed in claim 1 wherein the alkali-metal alcoholate has 1~5 carbon atoms.

6. The process as claimed in claim 1 wherein the temperature of the reaction tank is between 150~300° C. and the reaction pressure is between 2.5~8.4 MPa.

7. A process of preparing a sapogenin according to the formula:

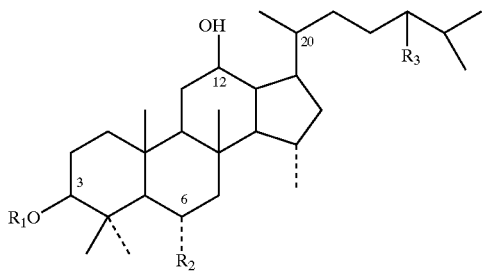

wherein $R_1$ is H; or glc, $R_2$ is H or OH, $R_3$ is H or OH; and when $R_1$, $R_2$, and $R_3$ are H, there are double bonds at positions 20(21) and 24(25); and when $R_1$ is H, $R_2$, is OH and $R_3$ is OH, there are double bonds at positions 20(22) and 25(26); and when $R_1$ is glc, $R_2$ is H and $R_3$ is H, there are double bonds at positions 20(21) and 24(25); which process comprises:

producing a ginsenoside extract from plants selected from the group consisting of panax ginseng, panax quinguefol and panax notoginseng, and proceeding according to the following steps:
(a) mixing the ginsenoside extract with water;
(b) mixing the ginsenoside extract and water with a short-chain (1–5 carbon) alkali-metal alcoholate solution or a hydroxide-ethanol solution to produce a mixture; and
(c) placing the resultant mixture in a reaction tank so that the resultant mixture can undergo chemical reactions under high temperature and high pressure effective to produce sapogenins therefrom; and
(d) after the reaction is completed, collecting an intermediate product of a mix of gensenosides and sapogenins from the ethanol mixture; and
(e) separating the desired sapogenins from the intermediate saponin-sapogenin mixture by silica-gel-column chromatography.

8. A process of preparing a sapogenin according to the formula:

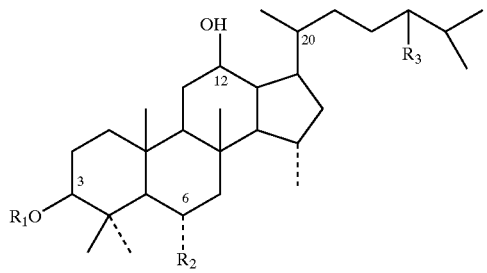

wherein $R_1$ is H or glc, $R_2$ is H or OH, $R_3$ is H or OH; and when $R_1$, $R_2$, and $R_3$ are H, there are double bonds at positions 20(21) and 24(25); and when $R_1$ is H, $R_2$, is OH and $R_3$ is OH, there are double bonds at positions 20(22) and 25(26); and when $R_1$ is glc, $R_2$ is H and $R_3$ is H, there are double bonds at positions 20(21) and 24(25); which process comprises:

producing a ginsenoside extract from plants selected from the group consisting of panax ginseng, panax quinguefol and panax notoginseng, and proceeding according to the following steps:
(a) mixing the ginsenosides extract with ethanol;
(b) mixing the extract and ethanol with alkali-metal alcoholates solution to produce a mixture, and
(c) placing the resultant mixture in a reaction tank so that the resultant mixture can undergo chemical reactions under high temperature and high pressure effective to produce sapogenins therefrom;
(d) after the reaction is completed, collecting an intermediate product of a mix of gensenosides and sapogenins from the ethanol mixture; and
(e) separating the desired sapogenins from the intermediate saponin-sapogenin mixture by silica-gel-column chromatography.

9. The process as claimed in claim 1 wherein the temperature of the reaction tank is between 240–300° C. and the reaction pressure is between 3.5–8.4 MPa.

* * * * *